United States Patent [19]

Clark

[11] Patent Number: 5,210,913
[45] Date of Patent: May 18, 1993

[54] INVASIVE LINE SEPARATOR

[75] Inventor: Deborah K. Clark, Palm Bay, Fla.

[73] Assignee: 2-RN Corporation

[21] Appl. No.: 791,585

[22] Filed: Nov. 12, 1991

[51] Int. Cl.[5] .......................... A44B 21/00; F16L 3/00
[52] U.S. Cl. ........................................ 24/518; 24/517; 24/543; 248/68.1
[58] Field of Search ................. 24/518, 517, 543, 489, 24/507; 40/315, 300, 633; 128/DIG. 26; 248/68.1; 251/6, 10

[56] References Cited

U.S. PATENT DOCUMENTS

| | | | |
|---|---|---|---|
| 1,987,159 | 1/1935 | Rasmussen | 24/517 |
| 2,214,030 | 9/1940 | Pereles | 40/315 |
| 3,050,578 | 8/1962 | Huebner | 24/335 |
| 4,198,989 | 4/1980 | Hawke et al. | 128/DIG. 26 |
| 4,308,642 | 1/1982 | Heyman | 248/68.1 |
| 4,775,121 | 10/1988 | Carty | 248/68.1 |
| 4,795,429 | 1/1989 | Feldstein | 128/DIG. 26 |
| 4,881,705 | 11/1989 | Kraus | 248/68.1 |
| 4,971,271 | 11/1990 | Sularz | 248/68.1 |
| 4,988,062 | 1/1991 | London | 128/DIG. 26 |
| 5,056,248 | 10/1991 | Blanchard | 24/543 |

FOREIGN PATENT DOCUMENTS 3441302  4/1986  Fed. Rep. of Germany ........ 24/543

OTHER PUBLICATIONS

Sterile Adhesive Organizer, Surgical Concepts, Inc. Div., KAPP Surgical Cleveland, Ohio 44128, 1991.

*Primary Examiner*—Victor N. Sakran
*Attorney, Agent, or Firm*—Evenson, Wands, Edwards, Lenahan & McKeown

[57] ABSTRACT

An invasive line separator comprises first and second plates of translucent plastic, which are hinged together so that they fold against one another in a face-to-face configuration. The first plate has a plurality of spaced apart, parallel channels that are sized and configured to receive and engage respective sections of invasive line, so that when the lines are placed within the channels they lie beneath the planar surface of the plate. This allows the hinged second plate to be folded into abutment with and provide a cover for channels of the first plate, without constricting invasive lines placed in the channels. The first plate also contains one or more slots alongside an edge, to accommodate straps for securing the separator to an adjacent structure, such as a bed rail. With the hinged plates folded together, any sections of invasive line that have been arranged within the grooves are securely retained in the first plate by second plate. On the side of the second plate opposite the side facing the channels in the first plate one or more surface regions may be configured to receive adhesive strips of labelling material for identifying each line. The labelling surface regions are arranged to be parallel with and overlie the channels in the first plate when the first and second plates are folded together.

10 Claims, 1 Drawing Sheet

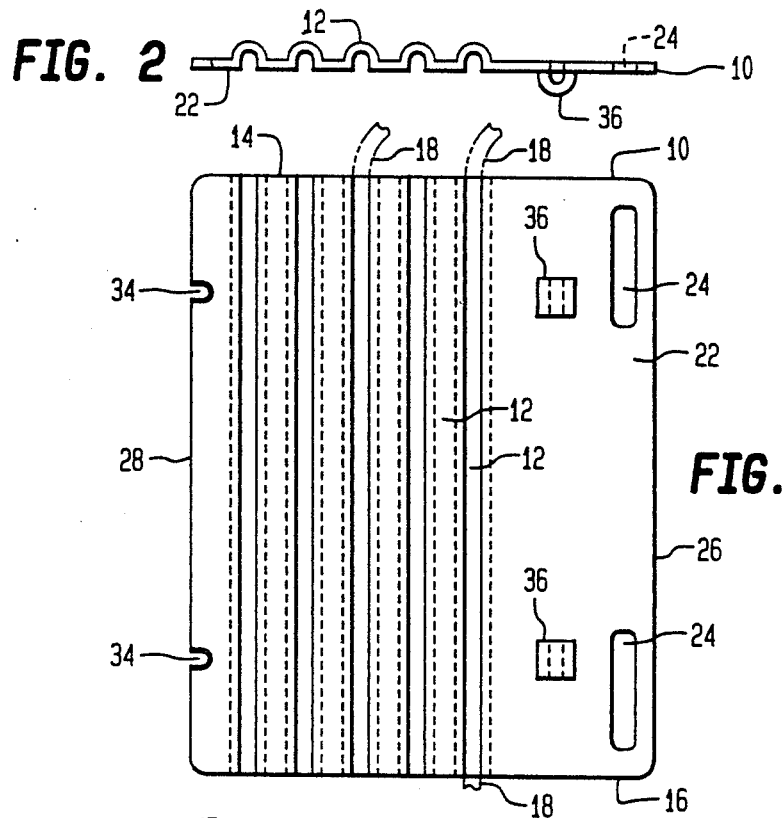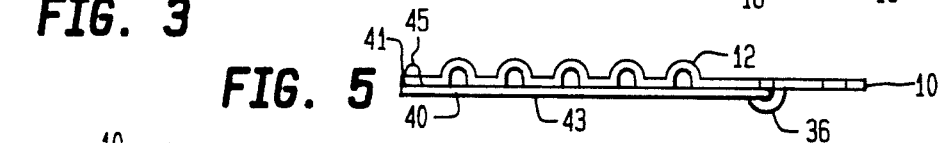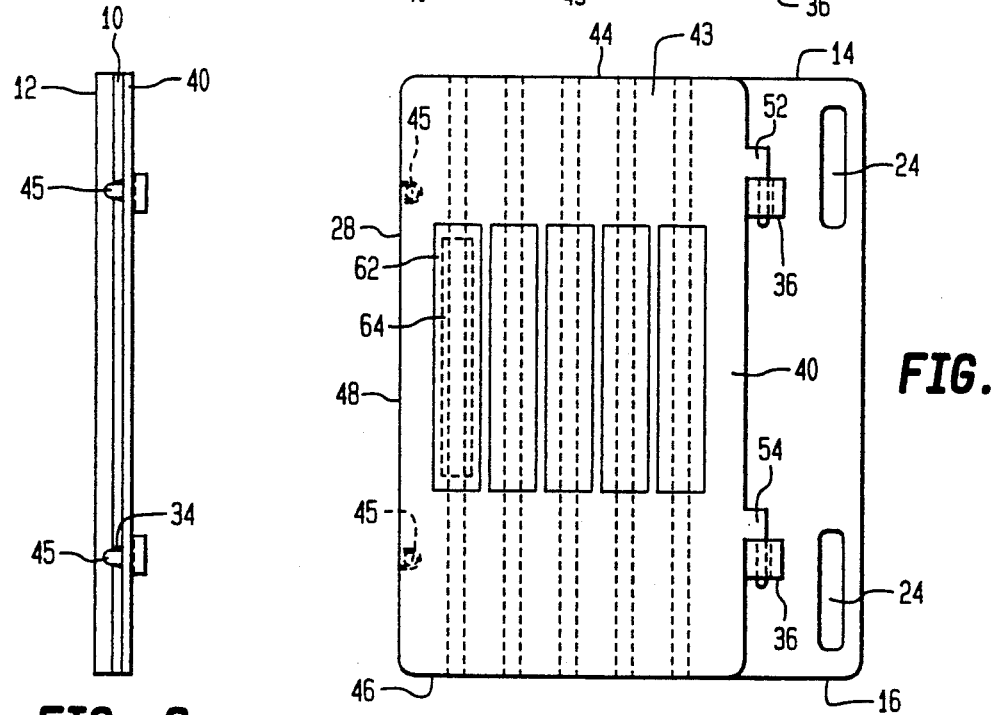

INVASIVE LINE SEPARATOR

FIELD OF THE INVENTION

The present invention relates in general to medical appliances and is particularly directed to a device for organizing, separating and maintaining identification of a plurality of invasive lines of a patient.

BACKGROUND OF THE INVENTION

Medical treatment of a patient often requires the use of a plurality of invasive lines which may be of differing lengths and which may be connected with the patient at a variety of body entry sites. Because these lines are flexible and may be dispersed throughout an are where the patient is being treated (e.g. a hospital bed or stretcher), they are subject to becoming tangled and disconnected from the patient and attendant medical equipment. Conventionally used schemes to deal with this problem (what is often referred to by hospital personnel as a 'spaghetti' mess) have included taping the lines to a board or the patient's bed, pinning the lines to the bed, and clipping the lines to hemostats to be clipped to the patient, none of which has proven satisfactory. A more complicated and still unacceptable proposal to organize and identify invasive lines is described in U.S. Pat. No. 4,988,062 to R. A. London and involves the use of a multi-slotted manifold that is configured to be mounted upon a patient support surface, such as the patient's bed, and held in place or confined beneath the patient's headrest. Such a manifold structure merely provides a fixed bed-to-equipment interface from which multiple invasive lines fan out to the patient, on the one hand, and to attendant medical equipment external to the bed, on the other hand. Elsewhere, on and around the patient, the invasive lines are still subject to becoming kinked, snagged, tangled and disconnected from the patient, particularly if the patient is moved (e.g. rolled over).

SUMMARY OF THE INVENTION

In accordance with the present invention, the above described drawbacks of conventional solutions to the problem of providing an orderly separation and identification of invasive lines anywhere around the patient is successfully addressed by a new and improved invasive line separator structure that enables medical personnel to easily and readily establish the physical location of any portion of one or more of a plurality of invasive lines relative to the patient and the patient's surroundings. For this purpose, the present invention employs first and second plates preferably made of lightweight but sturdy material such as translucent plastic, the first and second plates being hinged together so that they fold against one another in a face-to-face configuration. The first plate has a plurality of spaced apart, parallel channels or grooves that run the length of the plate between opposite end edges of the plate. The grooves or channels are sized and configured to receive and engage respective sections of invasive line, so that when the lines are placed within the channels they lie beneath the planar surface of the plate. This allows the hinged second plate to be folded into abutment with and provide a cover for channels of the first plate, without touching or deforming (e.g. crimping) invasive lines that have been placed in the channels. The first plate also contains one or more slots alongside an edge, to accommodate one or more tie members or straps for securing the separator to an adjacent structure, such as a bed rail.

With the hinged plates folded together, any sections of invasive line that have been arranged within the grooves are securely retained in the first plate by second plate. On the side of the second plate opposite the side facing the channels in the first plate one or more surface regions may be configured to receive adhesive strips of labelling material (e.g. peelable labels), for identifying each line. The labelling surface regions are arranged to be parallel with and overlie the channels in the first plate when the first and second plates are folded together, thereby permitting medical personnel to quickly identify each line merely by reading the separator labelling.

Preferably, the hinged plates are sized proximate to the size of a human hand, so that the separator is relatively compact, facilitating its use anywhere around the patient, without the danger of interfering with the functional use of the invasive lines themselves or other medical appliances. In this regard, because of its size and configuration, the invasive line separator of the present invention can be secured so as not to come in contact with the patient's skin, thereby preventing possible irritation of a patient who has a sensitivity to plastic and making sterilization of the device unnecessary.

BRIEF DESCRIPTION OF THE DRAWINGS

FIGS. 1, 2 and 3 are respective plan, end and side views of a channelled plate of the invasive line separator of the present invention; and FIGS. 4, 5 and 6 are respective plan, end and side views of the invasive line separator of the present invention, showing a cove plate folded into face-to-face abutment with the channeled plate for confining invasive lines.

DETAILED DESCRIPTION

Referring now to FIGS. 1, 2 and 3, respective plan, end and side views of a first plate 10 of the invasive line separator of the present invention are shown. Plate 10 is preferably made of a lightweight durable translucent plastic and has a generally rectangular configuration in plan. A typical thickness of plate 10 may be on the order of ninety mils, while its length and width may be on the order of five and four inches, respectively, thereby realizing a relatively compact plate structure proximate that of the human hand and permits easy handling. It should be observed, however, that these and other dimensions are merely for purposes of an illustrative example and are not limitative of the invention. Because the hinged plates are sized proximate to the size of a human hand, the separator is relatively compact, facilitating its use anywhere around the patient, without the danger of interfering with the functional use of the invasive lines themselves or other medical appliances. In addition, as noted previously, because of its size and configuration, the invasive line separator of the present invention can be secured so as not to come in contact with the patient's skin, thereby preventing possible irritation of a patient who has a sensitivity to plastic and making sterilization of the device unnecessary.

Plate 10 has a plurality of spaced apart, parallel channels or grooves 12 that run the length of the plate between opposite end edges 14 and 16. Channels 12 are sized and configured to receive and engage respective sections 18 of invasive line, so that when the lines 18 are placed within the channels 12 they lie beneath the planar surface 22 of the plate. This allows a second plate that is hinged with the plate 10 to be folded into abutment with and provide a protective, confining cover for the channels, without deforming (e.g. crimping) invasive lines that have been placed in the channels, so that the invasive lines are maintained spaced apart from one another to prevent tangling of the lines.

Plate 10 also contains one or more (elongated) slots 24 alongside an edge 26, to accommodate one or more tie members or straps 32, securing the separator to an adjacent structure, such as a bed rail, IV pole or patient's gown. For this purpose, respective lengths of eye and hook material (e.g. Velcro) straps may be used. Opposite edge 28 of plate 10 is shown as having a pair of notches 34 which are sized to engage posts 45 of a second plate (shown at 40 in FIGS. 4–6) which is joined to plate 10 by means of hinges members 36.

The hinged attachment of second plate 40 to plate 1 is shown in plan in FIG. 4 and in the respective end and side views of FIGS. 5 and 6, respectively. Plate 40 has a pair of end edges 44, 46 and side edges 47, 48. The width of plate 40 between parallel side edges 47, 48 is less than that of plate 10 so as to provide a clearance for slots 24 in plate 10, as shown in FIG. 4. Edge 47 has a pair of hinge flanges 52 that engage and are captured by hinge members 36 of plate 10, thereby permitting face 41 of plate 40 to be folded into and away from planar face-to-face abutment with face 22 of plate 10. Adjacent to edge 48, plate 40 has a pair of posts 4, that are located and sized to engage notches 34 in plate 10 when the plates are folded together, thereby retaining the plates in a closed condition, as shown in the side and end views of FIGS. 5 and 6. Thus, with hinged plates 10 and 40 folded together, any sections of invasive line 18 that have been arranged within grooves 12 are, securely retained in spaced apart relationship in plate 10 by overlying second plate 40 so as to prevent tangling of the sections of invasive line.

On side 43 of plate 40 opposite side 41, which faces channels 12 in plate 10, one or more surface regions 62 may be configured to receive adhesive strips 64 of labelling material (e.g. peelable labels), for identifying each line in the underlying groove. As shown in FIG. 4, these labelling surface regions 62 are arranged to be parallel with channels 12 in plate 10 when the plates are folded together, thereby permitting medical personnel to quickly identify each line merely by reading the respective separator labels.

Because of its multi-channel configuration and compact size, the invasive line separator structure of the present invention is not only capable of organizing a plurality of invasive lines used for respectively different invasive applications, but may be used to physically gather and retain successive lengths of the same invasive line in a back and forth looped fashion, so that a long section of tubing can be retained in a secure, nested manner alongside the patient, such as during movement of a patient in a wheelchair.

As will be appreciated from the foregoing description of the present invention, the drawbacks of conventional schemes for handling invasive lines around a patient are successfully addressed by an invasive line separator structure that enables medical personnel to easily and readily establish the physical location of any portion of one or more of a plurality of invasive lines relative to the patient and the patient's surroundings. The lightweight but sturdy, hinged plate configuration of the invention facilitates rapid placement and maintains an orderly separation of respective sections of invasive line, so that the lines are not only captured within the channels of one of the plates of the separator but the ar protected and identified by the overlying second plate.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed:

1. A device for organizing and separating a plurality of sections of patient treatment tubing relative to a patient and the patient's surroundings, a respective section of patient treatment tubing, comprising:

a first plate having a first, generally flat surface in which are formed a plurality of longitudinal channels that extend between first and second ends of said first plate in a generally linear parallel arrangement and are spaced apart from one another by generally flat surfaced longitudinal land areas of said first plate therebetween, said longitudinal channels being sized and configured to receive respective sections of patient treatment tubing, so that when sections of tubing are placed within said longitudinal channels, said sections of tubing lie beneath said first surface of said first plate and are retained thereby in a generally longitudinal parallel arrangement; and a second plate having a first generally flat surface and being fixedly engageable with said first plate so that the first generally flat surface of said second plate, when brought into face-to-face abutment with the generally flat surfaced longitudinal land areas of the first surface of said first plate, provides a cover for said channels of said first plate between said generally flat surfaced longitudinal land areas of said first surface of said first plate, without effectively constricting sections of tubing placed in the longitudinal channels of said first plate, and maintaining said sections of tubing spaced apart from one another to prevent tangling of said tubes.

2. A device according to claim 1, wherein said first and second plates are made of translucent material and wherein said second plate contains one more labelling surface regions configured to receive labelling material for identifying respective sections of tubing confinement in channels of said first plate, said labelling regions being arranged to be parallel with and overlie the longitudinal channels in said first plate when the first and second plates are brought into face-to-face abutment with one another.

3. A device according to claim 2, wherein said first plate further comprises one or more slots alongside an edge thereof, accommodating one or more tie members or straps for securing the device to an adjacent structure.

4. A device according to claim 1, wherein said first and second hinged plates are sized proximate to the size of a human hand, so that said structure is relatively compact, so as to not interfere with the functional use of the invasive lines themselves or other medical appliances.

5. A device according to claim 1, further including engaging retention members which maintain the first surface of said first and second plates in face-to-face abutment when the plates are brought together.

6. A method for organizing and separating a plurality of sections of invasive line used for treatment of a patient, relative to a patient or the patient's surroundings, comprising the steps of:

(a) providing an invasive line confinement device, said device being comprised of a first plate having a first, generally flat surface in which are formed a plurality of longitudinal channels that extend between first and second ends of said first plate in a generally linear parallel arrangement and are spaced apart from one another by generally flat surfaced longitudinal land areas of said first plate therebetween, said longitudinal channels being sized and configured to receive respective sections of invasive line, so that when sections of invasive line are placed within said longitudinal channels, said sections of invasive line lie beneath said first surface of said first plate and are retained thereby in a generally longitudinal parallel arrangement, and a second plate having a first generally flat surface and being fixedly engageable with said first plate, so that the first generally flat surface of said second plate, when brought into face-to-face abutment with the generally flat surfaced longitudinal land areas of the first surface of said first plate, provides a cover for said channels of said first plate between said generally flat surfaced longitudinal land areas of said first surface of said first plate, without effectively constricting sections of invasive line placed in the longitudinal channels of said first plate, and maintaining said sections of invasive line spaced apart from one another to prevent tangling of said sections of invasive line.

(b) placing at least one section of invasive line in at least one channel of said first plate and bringing said first surface of said second plate into face-to-face abutment with said first surface of said first plate, so that said at least one section of invasive line is confined within said at least one channel of said invasive line confinement device.

7. A method according to claim 6, further comprising the step (c) of attaching said invasive line confinement device to member that effectively limits movement of said invasive line confinement device.

8. A method according to claim 7, wherein said first plate further comprises one or more slots alongside an edge thereof, accommodating one or more tie members for securing the device to an adjacent structure, and step (c) comprises attaching said invasive line confinement device to said adjacent structure by way of said one or more tie members so as to effectively limit movement of said invasive line confinement device.

9. A method according to claim 8, wherein said second plate contains one or more labelling surface regions configured to receive labelling material for identifying respective invasive lines confined in channels of said first plate, said labelling surface regions being arranged to be parallel with and overlie the channels in said first plate when the first and second plates are brought into face-to-face abutment, and wherein said method further comprises the step (d) of placing invasive line identification markings on said one or more labelling surface regions.

10. A method according to claim 6, wherein said first and second plates include engaging retention members for maintaining said first and second plates in face-to-face abutment.

* * * * *